United States Patent [19]

Ohsaki et al.

[11] Patent Number: 5,354,918
[45] Date of Patent: Oct. 11, 1994

[54] HIGHLY PURE MONOALKYLPHOSPHINE

[75] Inventors: Hiromi Ohsaki; Kazuyuki Asakura, both of Joetsu; Masashi Sugiya, Tokyo; Yutaka Demura; Tomio Yanai, both of Kohriyama, all of Japan

[73] Assignees: Shin-Etsu Chemical Co., Ltd.; Nippon Chemical Industrial Co., Ltd., both of Japan

[21] Appl. No.: 91,363

[22] Filed: Jul. 15, 1993

[30] Foreign Application Priority Data

Jul. 17, 1992 [JP] Japan .................................. 4-190487
Nov. 9, 1992 [JP] Japan .................................. 4-298629
Mar. 12, 1993 [JP] Japan .................................. 5-51806
Mar. 22, 1993 [JP] Japan .................................. 5-61775

[51] Int. Cl.$^5$ ............................................. C07F 9/50
[52] U.S. Cl. .................................................. 568/8
[58] Field of Search ...................................... 568/8

[56] References Cited

U.S. PATENT DOCUMENTS 2,584,112  2/1952  Brown .
4,922,025  5/1990  Hoelderich et al. ................. 568/14
5,041,676  8/1991  Hofmann ............................ 568/8

OTHER PUBLICATIONS

Hoff et al., Journal of Organic Chemistry, (24) pp. 356–359, 1959.
Chemical Abstracts, vol. 117, 1992, Columbus, Ohio, US; abstract No. 171693s, & JP-A-04 149 187 (Nippon Mining Co., Ltd.).

*Primary Examiner*—Johann Richter
*Assistant Examiner*—Margaret J. Page
*Attorney, Agent, or Firm*—Parkhurst, Wendel & Rossi

[57] ABSTRACT

The method for preparing a monoalkylphosphine of high purity comprises reacting phosphine and an alkene in the presence of an anhydrous alkanesulfonic acid as a catalyst in a solvent having a boiling point higher than that of the monoalkylphosphine produced. The resulting monoalkylphosphine is brought into contact with an alkali solution to remove the catalyst, which is a sulfur atom-containing compound, remaining in the solution. The reaction solution from which the remaining catalyst is removed is then brought into contact with alkali metal hydrides or alkaline earth metal hydrides to eliminate any moisture remaining in the reaction solution. The alkali metal hydride is preferably sodium hydride or lithium aluminum hydride, while the alkaline earth metal hydride is preferably calcium hydride. The resulting monoalkylphosphine is isolated through distillation and the compound in a gaseous or liquid state is brought into contact with and passed through a layer of active carbon to remove other impurities present therein.

9 Claims, No Drawings

HIGHLY PURE MONOALKYLPHOSPHINE

BACKGROUND OF THE INVENTION

The present invention relates to a highly pure monoalkylphosphine and a method for preparing the same. The highly pure monoalkylphosphine is useful as a material for use in the epitaxial growth of compound semiconductors.

Recently, compound semiconductors have widely been used in various fields such as light emitting diodes, semiconductor lasers and high electron mobility transistors (HEMT). As a method for preparing a compound semiconductor, there has widely been used an epitaxial crystal-growth technique such as a Metalorganic Chemical Vapor Deposition (MOCVD) method. Compound semiconductors prepared by such an epitaxial crystal-growth technique include, for instance, Group III-V compound semiconductors in which phosphine containing a phosphorus atom is often used as a source for phosphorus atom, a Group V element.

Phosphines are highly toxic and suffer from a problem of safety. Recently, there has been proposed the use of monoalkylphosphorous atom-containing compounds as sources of phosphorus atom, one of group V elements, and they have attracted special interest recently as a substitute for phosphine since the use thereof permits the formation of epitaxial growth films having a low carbon content as an impurity and they are less toxic than phosphine.

As methods for preparing monoalkylphosphines, there have been known, for instance, those comprising reducing phosphonium chloride or phosphorous acid (see, for instance, Z. anorg. allg. Chem., 1978, 443, p. 42). However, these methods never permit the preparation of a highly pure monoalkylphosphines since they employ metallic catalysts in the reduction and suffer from a problem of contamination with metal impurities. Moreover, they include a production process requiring a long time period which results in a decrease of the yield of a desired product and makes the practice thereof in an industrial scale unfavorable. In addition, J. Org. Chem., 1959, 24, p. 356 discloses another method for preparing a monoalkylphosphine, which comprises reacting phosphine with an olefin. This method makes the mass production of monoalklphosphines substantially easier. However, this method includes a reaction in an aqueous system since it requires the use of an aqueous solution of an alkanesulfonic acid as a catalyst and accordingly, the method is liable to cause the formation of secondary and tertiary phosphine compounds as by-products whose removal is quite difficult and which inevitably lead to a decrease in the yield of the desired product.

Moreover, if impurities originated from the catalyst used are present in the resulting alkylphosphine, the compound semiconductor formed from a crystal prepared through the epitaxial growth of the phosphine does not exhibit desired electrical and optical properties at all. For this reason, an alkylphosphine for use in the production of a compound semiconductor is in general purified by high precision distillation. However, such high precision distillation in itself has not yet permitted the preparation of any monoalkylphosphine having a purity required for the production of a compound semiconductor.

SUMMARY OF THE INVENTION

The present invention has been completed for eliminating the foregoing drawbacks associated with the conventional techniques and accordingly, an object of the present invention is to provide an industrially effective method for efficiently and safely preparing, in high production efficiency, a monoalkylphosphine useful as a starting material for epitaxial crystal-growth, which has a high purity level commonly required for the starting material used in the production of a compound semiconductor.

The inventors of this invention have conducted various studies on the basis of the foregoing facts and, as a result, have found out a method for preparing a monoalkylphosphine of high purity in a high yield. Thus, the inventors of this invention have completed the present invention.

The method for preparing a monoalkylphosphine of high purity according to the present invention comprises reacting phosphine and an alkene in the presence of a catalyst comprising at least one member selected from the group consisting of anhydrous alkanesulfonic acids represented by the following general formula (I):

$$R-SO_2H \hspace{2cm} (I)$$

(wherein R represents an alkyl group having 1 to 4 carbon atoms) in an organic solvent having a boiling point higher than that of the monoalkylphosphine produced.

In particular, the reaction solution obtained through the foregoing reaction is preferably brought into contact with an alkali solution for the removal of the catalyst remaining therein. It is further preferred that, after contacting the reaction solution with the alkali solution, the reaction solution is brought into contact with a hydride of alkali metal and/or a hydride of alkaline earth metal since this ensures the removal of the remaining water in the reaction solution. The resulting monoalkylphosphine in a gaseous state or in the form of a solution is preferably brought into contact with and passed through an active carbon layer to thus remove other coexisting impurities present therein.

DESCRIPTION OF THE PREFERRED EMBODIMENTS

Phosphine used as a starting material in the method for preparing a highly pure monoalkylphosphine according to the present invention may be those obtained by any method, but preferably used are highly pure products each having a very low content of metallic and/or oxidative impurities.

Alkenes used as another starting material are linear or branched unsaturated aliphatic hydrocarbons preferably having 2 to 16 carbon atoms. Specific examples thereof include isobutene, 2-methyl-1-butene, 2-ethyl-1-butene, 2-methyl-1-pentene, 2-methyl-1-hexene, 2,3,3-trimethyl-1-butene, 2,3-dimethyl-1-hexene, 2-ethyl-1-hexene, isooctene, 2-methyl-1-heptene, 2,2,4-trimethyl-1-pentene, 2,4-dimethyl-1-hexene, 2,2,4-trimethyl-1-hexene, 2-methyl-1-nonene, triisobutylene and tetraisobutylene.

One of the features of the present invention is to use a reaction solvent selected from those each having a boiling point higher than that of the resulting monoalkylphosphine. This is because the difference between the boiling points of the monoalkylphosphine and the solvent used permits the recovery of the monoalkylphosphine of high purity through distillation of the reaction solution or optional precision distillation performed after the completion of the reaction. Such reaction solvents are preferably saturated aliphatic hydrocarbons, in particular those having 8 to 18 carbon atoms. Specific examples thereof are n-octane, isooctane, n-nonane, n-decane, n-tridecane, n-tetradecane, n-hexadecane and n-octadecane. Moreover, mixed solvents such as n-paraffin may likewise preferably be used.

Catalysts used in the method of the invention are preferably lower alkanesulfonic acids having 1 to 4 carbon atoms represented by the following general formula (I):

$$R-SO_3H \tag{I}$$

(wherein R represents an alkyl group having 1 to 4 carbon atoms) and specific examples thereof include methanesulfonic acid, ethanesulfonic acid, propanesulfonic acid and butanesulfonic acid. These lower alkanesulfonic acids may be used alone or in any combination and they must be in the anhydrous state. These lower alkanesulfonic acids are in general unstable and, therefore, they are preferably purified by, for instance, distillation prior to practical use.

According to another feature of the present invention, the foregoing reaction is performed in a non-aqueous system. The reaction performed in a non-aqueous system makes it possible to inhibit the formation of secondary or tertiary alkylphosphine compounds which are inevitably formed during the reaction as by-products if it is performed in an aqueous system. Moreover, the anhydrous alkanesulfonic acid catalyst has an ability of dehydration in itself and accordingly, it can adsorb a trace amount of water present in the reactor. This results in the complete prevention of any contamination of the reactor with water, makes the reaction in the non-aqueous system complete and in turn permits the preparation of highly pure monoalkylphosphines.

The reaction conditions vary depending on various factors such as the properties of the reactants used and the kinds of solvents and/or catalysts selected, but the reaction is preferably performed under pressure in a pressure vessel such as an autoclave, at a molar ratio: alkene/phosphine ranging from 1:1 to 1:5, preferably 1:1 to 1:2.5. In addition, the reaction temperature in general ranges from room temperature to 100° C., preferably 60° to 80° C. and the reaction time in general ranges from 1 to 24 hours, preferably 2 to 10 hours.

The starting materials are introduced into a reaction vessel after purging the reaction vessel and replacing the atmosphere in the reaction vessel with an inert gas such as nitrogen or helium. In this respect, it is desirable to introduce, into the reaction vessel, the starting materials in the order of a reaction solvent, an alkene and phosphine for preventing any self-polymerization of the alkene. Then the temperature of the reaction mixture is elevated to a desired level and a catalyst is supplied to the reaction vessel under pressure.

After the reaction is completed and the reaction solution is cooled down to room temperature, the excess phosphine is replaced with an inert gas, followed by allowing the reaction solution to stud and separation of the alkanesulfonic acid as the catalyst used.

The method discussed above permits the preparation of a monoalkylphosphine having a substantially high purity. The purity of the monoalkylphosphine thus obtained can be further enhanced if it is treated in the following manner.

An alkali solution is added to the organic phase to remove the sulfur atom-containing compound used as the catalyst. As the alkali solution, there may be used, for instance, an aqueous solution of an alkali compound selected from the group consisting of hydroxides of Group Ia metals, hydroxides of Group IIa metals, ammonia and amine type compounds. Among these aqueous alkali solutions, particularly preferred are aqueous solutions of hydroxides of Group Ia metals whose concentration preferably ranges from 0.1 to 3N. The term "amine type compounds" herein used includes aliphatic amine compounds each carrying an alkyl group having a carbon atom number of not more than 4, urea and tetramethyl urea, i.e., a derivative of urea. Each of these aqueous alkali solutions may comprise at least one of these alkali compounds. In particular, preferably used are aqueous solutions of hydroxides of Group Ia metals having concentrations ranging from 0.5 to 2N. The alkali aqueous solution is preferably prepared from a highly pure alkali compound and highly pure water. After addition of such an alkali solution, the reaction solution is stirred at ordinary temperature or under heating.

The amount of the aqueous alkali solution to be added to the reaction solution preferably ranges from 10 to 2000 parts by weight per 100 parts by weight of the monoalkylphosphine formed during the reaction.

The sulfur atom-containing compound used as the catalyst can satisfactorily be removed through the use of the method detailed above.

More specifically, the alkali aqueous solution is added to the reaction solution, followed by stirring and allowing it to stand to separate the aqueous alkaline phase. In this respect, the foregoing steps, i.e., the addition of an alkali aqueous solution, the stirring and the separation of the aqueous alkaline phase, may be repeated over a desired time.

Then an alkali metal hydride and/or an alkaline earth metal hydride are added to the remaining organic phase to remove the moisture remaining in the organic phase.

The metal hydrides usable in the present invention include, for instance, hydrides of Group Ia metals and/or hydrides of Group IIa metals. Specific examples thereof are lithium hydride, sodium hydride, potassium hydride, rubidium hydride, cesium hydride, calcium hydride, strontium hydride, barium hydride and lithium aluminum hydride.

In the dehydration method which utilizes a metal hydride, the metal hydride is added to the organic phase and then the mixture is stirred at ordinary temperature or under heating. The amount of the metal hydride to be added ranges from 1 to 10 parts by weight and preferably 3 to 5 parts by weight per 100 parts by weight of the organic phase. After completion of the dehydration treatment, the excess metal hydride may be removed through filtration or by extracting the resulting monoalkylphosphine through distillation, with the latter method, i.e., the separation through distillation of the monoalkylphosphine formed being preferred.

The resulting monoalkylphosphine can be recovered by first subjecting the organic phase to simple distillation at ordinary pressure and then to optional precision distillation.

The product obtained through the reaction of phosphine with an alkene in a solvent is passed through a column packed with active carbon to remove various impurities such as compounds containing elephants such as sulfur, silicon and oxygen; compounds containing metals such as cadmium, magnesium, calcium, iron, manganese and arsenic; and the hydrocarbon compound used as the reaction solvent and to thus recover the desired monoalkylphosphine product of high purity substantially free of these various impurities.

The active carbon used in the present invention is not restricted to specific ones and may be those prepared from, for instance, palm husk, coal pitch, petroleum pitch and sawdust as starting materials. Moreover, the active carbon must not have any particular shape or form, but it is preferably a particulate one having a particle size ranging from 10 to 80 mesh while taking handling properties and easiness of purification operations into consideration. In addition, fibrous active carbon (active carbon fibers) is highly practicable since a high adsorption rate can be anticipated. When practically using such an active carbon, it must be sufficiently dried to remove any moisture attached thereto as much as possible to prevent the reduction in the adsorption function and any oxidation and deterioration of the organophosphorous compound to be purified which leads to a decrease of the yield of the compound. To this end, the active carbon is, for instance, sufficiently heated at a temperature on the order of 250° to 300° C. prior to practical use.

The amount of the active carbon to be used varies depending on the amount of impurities to be removed or the kinds thereof, but in general ranges from 0.1 to 100 parts by weight per 100 parts by weight of the monoalkylphosphine produced, with the practically preferred amount thereof ranging from 10 to 50 parts by weight.

The method according to the present invention may be used for preparing a monoalkylphosphine carrying any alkyl group, but the method is applied particularly to the preparation of mono-1,1-dimethylpropylphosphine and mono-1,1-dimethylethylphosphine since they are suitably used as sources of phosphorus atom (Group V element) for use in making compound semiconductors.

As has been explained above in detail, the method for preparing a highly pure monoalkylphosphine according to the present invention allows the production of the intended highly pure compound, with safety and in a high yield, which is useful as a material for epitaxial crystal-growth of compound semiconductors and the method further permits effective removal of impurities co-existing in the reaction solution.

The present invention will hereinafter be described in more detail with reference to the following working Examples, but the present invention is by no means limited to these specific Examples.

EXAMPLE 1

To about 1 l volume autoclave of stainless steel, as a reaction vessel, whose atmosphere is replaced with an inert gas, there were added 100 g of n-decane (boiling point: 174° C.) as a solvent, 80 g (1.426 mole) of isobutylene as a reactant and 135.8 g (3.994 moles) of highly pure phosphine at room temperature. The pressure in the autoclave was controlled to 25 kg/cm$^2$. The temperature of the contents of the autoclave was elevated to 60° C. and then 137 g (1.426 mole) of methanesulfonic acid purified through simple distillation was introduced into the autoclave over about one hour using an injection pump. The pressure in the autoclave was lowered from 35 kg/cm$^2$ to 28 kg/cm$^2$. The reaction mixture was additionally ripened over one hour while maintaining the temperature thereof at 60° C. After completion of the reaction, the reaction mixture was cooled down to about 30° C., the excess unreacted phosphine was removed through evacuation and the atmosphere of the reaction system was replaced with nitrogen gas. The reaction product was withdrawn from the autoclave, followed by allowing it to stand at room temperature over a whole day and night and removal of the lower phase comprising the methanesulfonic acid through liquid-liquid separation.

The resulting n-decane phase was analyzed by gas chromatography and it was found that 57.8 g (conversion rate: 45.0% on the basis of isobutene) of mono-1,1-dimethylethylphosphine and that di- and tri-1,1-dimethylethylphosphines were not detected at all in the n-decane phase (selectivity: 100%).

The resulting n-decane phase was subjected to simple distillation at ordinary pressure and then to precision distillation at ordinary pressure. Thus, 35.8 g (yield: 27.9%) of mono-1,1-dimethylethylphosphine (boiling point: 54° C.) could be isolated and the product had a purity of 99.9% as determined by gas chromatography technique.

The product thus obtained was confirmed to be the intended mono-1,1-dimethylethylphosphine by FT-IR, $^1$H-NMR and GC-MS measurements. The product was likewise subjected to metal analysis using inductively coupled plasma (ICP) technique and the amounts of all the metals examined were found to be less than the detection limit of the technique. The moisture content of the product was determined using a Beckman micromoisture meter (Model 340) and found to be not more than 5 ppm.

Comparative Example 1

The same procedures used in Example 1 were repeated except that the amount of the highly pure phosphine used was changed to 141 g and that 197 g of an aqueous solution of methanesulfonic acid prepared by dissolving 137 g of methanesulfonic acid in 60 g of pure water was substituted for the purified methanesulfonic acid used in Example 1. The pressure in the autoclave was reduced from 36 kg/cm$^2$ down to 30 kg/cm$^2$. The reaction mixture was ripened over one hour while maintaining the temperature thereof at 60° C.

After completion of the reaction, the resulting n-decane phase was analyzed in the same manner used in Example 1 and the following results listed in Table 1 were observed.

TABLE 1

|  | Conversion Rate on the basis of Isobutene |
|---|---|
| mono-1,1-dimethylethylphosphine | 25% |
| di-1,1-dimethylethylphosphine | 12% |
| tri-1,1-dimethylethylphosphine | trace amount |

The results obtained in Example 1 and Comparative Example 1 clearly indicate that the selectivity of the method for mono-1,1-dimethylethyl phosphine is reduced due to the presence of moisture in the reaction system.

EXAMPLE 2

To a reaction vessel identical to that used in Example 1, there were added 100 g of n-tetradecane (boiling point: 253° C.) as a reaction solvent, 80 g (1.141 mole) of 2-methyl-1-butene as an alkene component and 97.0 g (2.853 moles) of highly pure phosphine at room temperature. As the reaction vessel was heated to 60° C., the pressure in the reaction vessel was increased up to 22 kg/cm$^2$. Ethanesulfonic acid (125.0 g; 1.141 mole) as a catalyst was introduced into the vessel under pressure over one hour and thereafter the same procedures used in Example 1 were repeated to give 25.8 g of mono-1,1-dimethylpropylphosphine (boiling point: 78° C.). The yield of the product was found to be 21.7% and the purity thereof was found to be 99.9% as determined by gas chromatography. The product was subjected to metal analysis using the ICP technique and the amounts of all the metals examined were found to be less than the detection limit of the technique. The moisture content of the product was also determined using a Beckman micromoisture meter (Model 340) and found to be not more than 5 ppm.

EXAMPLE 3

To an autoclave as a reaction vessel, there were added n-decane, isobutylene and highly pure phosphine in the same manner used in Example 1, followed by elevation of the temperature to 60° C. at a pressure of 25 kg/cm$^2$, addition of methanesulfonic acid to the reaction mixture to initiate the reaction of isobutylene with phosphine and ripening. After completion of the reaction, the reaction mixture was cooled, the excess unreacted phosphine was removed through evacuation and the atmosphere of the reaction system was replaced with nitrogen gas. The reaction solution was allowed to stand over a whole day and night and the lower phase comprising the methanesulfonic acid was removed through liquid-liquid separation.

To the resulting product, there was added 150 g of a 1N aqueous solution of sodium hydroxide followed by stirring over one hour, allowing the mixture to stand and separation into n-decane and aqueous phases. The resulting n-decane phase was analyzed by gas chromatography and it was found that 56.1 g (rate of conversion on the basis of isobutene: 43.7%) of mono-1,1-dimethylethylphosphine was present therein and that di- and tri-1,1-dimethylethylphosphine were not detected at all in the n-decane phase (selectivity: 100%). The resulting n-decane phase was subjected to simple distillation at ordinary pressure and then to precision distillation at ordinary pressure. Thus, 33.6 g (yield: 26.2%) of mono-1,1-dimethylethylphosphine (boiling point: 54° C.) could be isolated and the product had a purity of 99.9% as determined by gas chromatography technique.

The product thus obtained was confirmed to be the intended mono-1,1-dimethylethylphosphine by FT-IR, $^1$H-NMR and GC-MS measurements. The product was likewise subjected to metal analysis using the ICP technique and the amounts of all the metals examined were found to be less than the detection limit of the ICP technique. Moreover, the product was dispensed and added to an equal amount of a 1N aqueous solution of sodium hydroxide, followed by stirring, allowing to stand and ICP emission spectroscopic analysis. As a result, the content of sulfur was less than the detection limit of the ICP emission spectrometer used and thus the resulting product was considered to be substantially free of sulfur compounds.

EXAMPLE 4

The sulfur content of mono-1,1-dimethylethylphosphine obtained in Example 1 was determined in the same manner used in Example 3 and found to be 60 ppm.

The results obtained in Examples 3 and 4 clearly indicate that the use of an aqueous solution of sodium hydroxide was effective for the removal of sulfur-containing compounds.

EXAMPLE 5

To a 1 l volume autoclave as a reaction vessel whose atmosphere is replaced with an inert gas, there were added 120 g of isobutene, 100 g of n-decane and 120 g of phosphine. Then 140 g of methanesulfonic acid was added to the autoclave under pressure and the mixture was stirred for 2 hours while maintaining the temperature thereof at 60° C. to cause the reaction of isobutene with phosphine. The pressure in the autoclave was increased up to about 30 kg/cm$^2$ during the reaction. After completion of the reaction, the excess unreacted phosphine was removed through evacuation at the time when the reaction mixture was cooled down to about 30° C. The reaction solution thus obtained was analyzed by gas chromatography and it was found that mono-1,1-dimethylethylphosphine was present therein. The yield of the product was found to be 44.4% on the basis of isobutene.

When the reaction solution was allowed to stand, it was separated into an organic phase and an inorganic phase. The organic phase was isolated from the inorganic phase, followed by addition of a 1N aqueous solution of sodium hydroxide to the organic phase, stirring and washing the mixture. The resulting solution was again allowed to stand to separate it into an organic phase and an inorganic phase. The organic phase was isolated from the inorganic phase and stored, while the aqueous phase was subjected to ICP emission spectroscopic analysis. As a result, sulfur components were detected in the aqueous phase through the spectroscopic analysis. A series of operations, i.e., the addition of an aqueous solution of sodium hydroxide to the organic phase, the separation of the mixture into an organic and inorganic phases and the emission spectroscopic analysis, was repeated till sulfur components were not detected, any more, by the emission spectroscopic analysis. When sulfur components were not present in detectable amounts in the inorganic phase any more, water of high purity was added to the organic phase as the counterpart of the inorganic phase and then stirred to wash the organic phase. The mixture was allowed to stand to separate it into an organic phase and an aqueous phase. The organic phase was stored, while the aqueous phase was analyzed and as a result, the presence of sodium hydroxide was detected. A series of operations, i.e., the addition of quite highly pure water, the stirring for washing and the analysis of the aqueous phase, was repeated till sodium hydroxide was not detected in the aqueous phase any more.

After confirming the absence of sodium hydroxide in the aqueous phase in any detectable amount, 3.0 g of calcium hydride was added to the organic phase as the counterpart of the aqueous phase and the mixture was stirred for one hour at ordinary temperature. After the agitation at ordinary temperature, the mixture was refluxed under heating for additional one hour with stirring. Thereafter, the mixture was distilled to give 65.0 g of mono-1,1-dimethylethylphosphine.

Table 2 given below shows the amounts of impurities (given in the column entitled "Prior to Processing" in Table 2) present in the samples collected after the washing process with water of very high purity and before the addition of calcium hydride, which were detected by gas chromatography mass spectrometer; and the amounts thereof (given in the column entitled "After Processing" in Table 2) present in the sample obtained after the distillation and detected by the same apparatus.

TABLE 2

| Impurity | Butanol | Water |
| --- | --- | --- |
| Prior to Processing (ppm) | 1500 | 800 |
| After Processing (ppm) | trace amount | trace amount |

Mono-1,1-dimethylethylphosphine thus prepared and purified was used in epitaxial growth of a crystalline semiconductor. The resulting semiconductor was found to exhibit excellent electrical and optical properties.

EXAMPLE 6

The same procedures used in Example 5 were repeated to give mono-1,1-dimethylethylphosphine which was substantially free of both sulfur atom-containing components and sodium hydroxide in amounts detectable with ICP emission spectroscopic analysis. The resulting mono-1,1-dimethylethylphosphine (69.5 g) was brought into contact with 3.0 g of molecular sieve in the same manner used in Example 5. Table 3 given below shows the results obtained by analyzing the sample obtained before and after being contacted with the molecular sieve to check for the presence of impurities.

TABLE 3

| Impurity | Butanol | Water |
| --- | --- | --- |
| Prior to Processing (ppm) | 1400 | 750 |
| After Processing (ppm) | 900 | 50 |

The results observed in Examples 5 and 6 clearly indicate that alkali hydrides were quite effective for removing impurities from the reaction product of the present invention.

EXAMPLE 7

A reaction solution containing mono-1,1-dimethylethylphosphine was prepared in the same manner used in Example 5.

The resulting reaction solution was allowed to stand to separate into organic and aqueous phases without addition of a 1N aqueous solution of sodium hydroxide and then subjected to precision distillation to give 69.0 g of crude mono-1,1-dimethylethylphosphine.

A part of the crude mono-1,1-dimethylethylphosphine thus obtained was analyzed by an inductively coupled plasma (ICP) emission spectrometer and a gas chromatograph to determine the amounts of impurities, i.e., sulfur atom-containing components and metal components (Fe, Mg, Mn, Si, As) as well as hydrocarbons. The results thus obtained are listed in the following Table 4 as data obtained "Prior to Processing".

TABLE 4

| Impurity | n-decane | Fe | Mg | Mn | As | Si | S |
| --- | --- | --- | --- | --- | --- | --- | --- |
| Prior to Processing (ppm) | 0.5 | trace | trace | trace | trace | 15 | 259 |
| After Processing (ppm) | x | x | x | x | x | 2 | 76 | x: This means that each impurity was not detected by the device.

A glass tube having a size of 20 cm×1.5 cm⌀ was filled with 10 g of particulate active carbon of 30 to 60 mesh (available from Nishto Industry Co., Ltd.). Then a solution containing the foregoing crude mono-1,1-dimethylethylphosphine was passed through the glass tube at a flow rate of 5 l/hr at room temperature to give 45.0 g (0.50 mole) of the intended phosphine of high purity.

A part of the purified mono-1,1-dimethylethylphosphine was likewise analyzed by an ICP emission spectrometer and a gas chromatograph to determine the amounts of impurities. The results thus obtained are also listed in Table 4 as data obtained "After Processing".

The foregoing results indicate that active carbon permitted the substantial removal of almost all of the sulfur atom-containing hydrocarbons and various metal compounds as trace impurities through adsorption, which is beyond expectations derived on the basis of the usual concept of adsorption, and that active carbon also allowed the removal of the hydrocarbons which cannot be removed through the precision distillation.

EXAMPLE 8

The same procedures used in Example 7 were repeated except that synthetic zeolite 5A was substituted for the active carbon used in Example 7. The results thus obtained are listed in the following Table 5.

TABLE 5

| Impurity | n-decane | Fe | Mg | Mn | As | Si | S |
| --- | --- | --- | --- | --- | --- | --- | --- |
| Prior to Processing (ppm) | 0.7 | trace | trace | trace | trace | 14 | 260 |
| After Processing (ppm) | 0.6 | trace | trace | trace | trace | 13 | 255 |

The results obtained in Examples 7 and 8 clearly indicate that adsorbents such as active alumina and synthetic zeolite 5A did not permit the substantial removal, through adsorption, of the sulfur atom-containing hydrocarbons, metal compounds and hydrocarbons and that active carbon permitted efficient purification of mono-1,1-dimethylethylphosphine to a purity level generally required for the preparation of intermetallic compound semiconductors.

EXAMPLE 9

To an autoclave, there were added n-decane, isobutylene and highly pure phosphine in the same manner used in Example 1, followed by elevation of the temperature to 60° C. at a pressure of 25 kg/cm², addition of methanesulfonic acid to the reaction mixture to initiate the reaction of isobutylene with phosphine and ripening. After completion of the reaction, the reaction mixture was cooled, the excess unreacted phosphine was removed through evacuation and the atmosphere of the reaction system was replaced with nitrogen gas. The reaction solution was allowed to stand and the lower phase comprising the methanesulfonic acid was removed through liquid-liquid separation.

To the resulting product, there was added 150 g of a 1N aqueous solution of sodium hydroxide followed by stirring over one hour, allowing to stand and separation into organic and aqueous phases. The aqueous phase was repeatedly washed till the sulfur atom-containing components were not detected any more by the ICP emission spectrometry. Thereafter the phase was further washed with very pure water in the same manner till sodium was not detected any more.

The resulting n-decane phase was analyzed by gas chromatography and as a result, it was found that 56.1 g (rate of conversion on the basis of isobutene: 43.7%) of mono-1,1-dimethylethylphosphine was present therein and that di- and tri-1,1-dimethylethylphosphine were not detected at all in the n-decane phase (selectivity: 100%).

After allowing to stand to separate into organic and aqueous phases, 0.5 g of calcium hydride was added to the organic phase. The resulting organic solution was stirred at ordinary temperature for one hour and then refluxed under heating for one hour with stirring. Thereafter, it was subjected to simple distillation at ordinary pressure in the presence of an excess calcium hydride and then to precision distillation at ordinary pressure. Thus, 33.6 g (yield: 26.2%) of mono-1,1-dimethylethylphosphine (boiling point: 54° C.) could be isolated and the product had a purity of 99.9% as determined by gas chromatography technique.

A glass tube having a size of 20 cm × 1.5 cm⌀ was filled with 10 g of particulate active carbon of 30 to 60 mesh (available from Nisho Industry Co., Ltd.). Then a solution containing the foregoing crude mono-1,1-dimethylethylphosphine was passed through the glass tube at a flow rate of 5 l/hr at room temperature and thus 30.2 g of purified mono-1,1-dimethylethylphosphine was recovered through the lower end of the tube.

The product thus obtained was confirmed to be the intended mono-1,1-dimethylethylphosphine by FT-IR, $^1$H-NMR and GC-MS measurements. The product was likewise subjected to metal analysis using the ICP technique and the amounts of all the metals examined were found to be less than the detection limit of the ICP technique. The moisture content of the product was determined using a Beckman micromoisture meter (Model 340) and found to be not more than 5 ppm.

What is claimed is:

1. A method for preparing a monoalkcylphosphine of high purity comprising the steps of
   (a) reacting, in a non-aqueous system, phosphine and an alkene in the presence of a catalyst containing at least one anhydrous alkanesulfonic acid of the formula R—SO$_3$H where R is an alkyl group of 1 to 4 carbon atoms, in an organic solvent having a boiling point higher than the boiling point of the monoalkylphosphine prepared,
   (b) contacting the system of step (a) with an alkali solution to remove catalyst remaining in the system, and
   (c) recovering the monoalkylphosphine.

2. The method for preparing a monoalkylphosphine of high purity as set forth in claim 1 wherein the alkali solution is an aqueous solution of a compound selected from the group consisting of hydroxides of Group Ia metals, hydroxides of Group IIa metals, ammonia, and amine compounds.

3. The method for preparing a monoalkylphosphine of high purity as set forth in claim 1 wherein the alkali solution is an aqueous solution of sodium hydroxide.

4. The method for preparing a monoalkylphosphine of high purity as set forth in claim 1 wherein the system from which the remaining catalyst is removed is brought into contact with at least one hydride selected from the group consisting of alkali metal hydrides and alkaline earth metal hydrides to eliminate any moisture remaining in the reaction solution.

5. The method for preparing a monoalkylphosphine of high purity as set forth in claim 4 wherein the alkali metal hydride is at least one of sodium hydride and lithium aluminum hydride.

6. The method for preparing a monoalkylphosphine of high purity as set forth in claim 4 wherein the alkaline earth metal hydride is calcium hydride.

7. The method for preparing a monoalkylphosphine of high purity as set forth in claim 1 wherein the resulting monoalkylphosphine in a gaseous or liquid state is brought into contact with and passed through a layer of active carbon to remove impurities present therein.

8. The method for preparing a monoalkylphosphine of high purity as set forth in claim 7 wherein the impurity is at least one member selected from the group consisting of a compound containing at least one of sulfur, silicon and oxygen; a compound containing at least one of the metals selected from cadmium, magnesium, calcium, iron, manganese and arsenic; and the organic solvent.

9. The method for preparing a monoalkylphosphine of high purity as set forth in claim 1 wherein the monoalkylphosphine is mono-1,1-dimethylethylphosphine.

* * * * *